(12) United States Patent
Megremis et al.

(10) Patent No.: US 9,250,160 B2
(45) Date of Patent: Feb. 2, 2016

(54) METHOD AND APPARATUS FOR CHARACTERIZING HANDPIECES

(71) Applicant: American Dental Association, Chicago, IL (US)

(72) Inventors: Spiro John Megremis, Chicago, IL (US); Daniel Edward Halpin, Glen Ellyn, IL (US); Henry Lukic, Chicago, IL (US); Henry J. Shepelak, Jr., Lisle, IL (US); Victoria K. Ong, San Francisco, CA (US)

(73) Assignee: American Dental Association, Chicago, IL (US)

( * ) Notice: Subject to any disclaimer, the term of this patent is extended or adjusted under 35 U.S.C. 154(b) by 155 days.

(21) Appl. No.: 14/216,246

(22) Filed: Mar. 17, 2014

(65) Prior Publication Data

US 2014/0260707 A1  Sep. 18, 2014

Related U.S. Application Data

(60) Provisional application No. 61/790,395, filed on Mar. 15, 2013.

(51) Int. Cl.
*G01L 5/00* (2006.01)
*G01M 99/00* (2011.01)
*A61C 1/00* (2006.01)

(52) U.S. Cl.
CPC ........... *G01M 99/008* (2013.01); *A61C 1/0038* (2013.01); *G01L 5/0061* (2013.01)

(58) Field of Classification Search
None
See application file for complete search history.

(56) References Cited

U.S. PATENT DOCUMENTS

| | | | |
|---|---|---|---|
| 1,435,082 | A | 11/1922 | Reedy |
| 1,605,079 | A | 11/1926 | Simmons |
| 1,730,974 | A | 10/1929 | Higbee |
| 3,023,615 | A | 3/1962 | Bennett |
| 3,192,768 | A | 7/1965 | Hildebrandt |
| 3,210,992 | A | 10/1965 | Lacy et al. |
| 3,354,711 | A | 11/1967 | Seney |
| 3,598,999 | A | 8/1971 | Hofmeister |
| 3,717,205 | A | 2/1973 | Wilderman |

(Continued)

FOREIGN PATENT DOCUMENTS

| | | |
|---|---|---|
| EP | 0295223 | 12/1988 |
| JP | 06109565 | 12/1995 |
| WO | 2004036167 | 4/2004 |

OTHER PUBLICATIONS

Dyson, J.E. and Darvell, B.W., "Torque, power and efficiency characterization of dental air turbine handpieces", Journal of Dentistry, 27, 1999, pp. 573-586.

(Continued)

*Primary Examiner* — Robert R Raevis
(74) *Attorney, Agent, or Firm* — Banner & Witcoff, Ltd.

(57) ABSTRACT

An apparatus for characterizing the performance of air turbine handpieces including high speed dental handpieces and chucking devices in terms of speed, torque, power, and air consumption include an air or fluid supply source for the handpiece and various sensors to measure input, flow rate, temperature and pressure and output speed and forces on the output shaft of the handpiece. Data from the sensors is collected, collated, processed and recorded to continuously provide a record of the handpiece characteristics for purposes of evaluating efficiency, quality control, safety and compliance with standards.

8 Claims, 24 Drawing Sheets

(56) References Cited

U.S. PATENT DOCUMENTS

| | | |
|---|---|---|
| 3,829,052 A | 8/1974 | Flannelly |
| 4,135,812 A | 1/1979 | Kingsland |
| 4,137,974 A | 2/1979 | Decker |
| 4,148,218 A | 4/1979 | Knowles et al. |
| 4,236,696 A | 12/1980 | Hicks et al. |
| 4,545,543 A | 10/1985 | Plucknett |
| 4,632,388 A | 12/1986 | Schleffendorf |
| 4,856,325 A | 8/1989 | Tomita et al. |
| 4,939,939 A | 7/1990 | Vemmer |
| 4,960,001 A | 10/1990 | Vemmer |
| 4,973,291 A | 11/1990 | Mottate |
| 5,063,676 A | 11/1991 | Gerber |
| 5,076,104 A | 12/1991 | Glaesemann et al. |
| 5,150,799 A | 9/1992 | Long, Jr. |
| 5,282,580 A | 2/1994 | Kent |
| 5,335,527 A | 8/1994 | Nagai et al. |
| 5,540,041 A | 7/1996 | Campbell et al. |
| 5,667,465 A | 9/1997 | McCollum et al. |
| 5,945,602 A | 8/1999 | Ross |
| 5,957,359 A | 9/1999 | Paivinen |
| 6,032,448 A | 3/2000 | Baker et al. |
| 6,311,805 B1 | 11/2001 | Juan |
| 7,997,131 B2 | 8/2011 | Novak et al. |
| 2005/0042588 A1 | 2/2005 | Wallaker |
| 2007/0113699 A1 | 5/2007 | Khajepour et al. |

OTHER PUBLICATIONS

Dyson, J.E. and Darvell, B.W., "Flow and free running speed characterization of dental air turbine handpieces", Journal of Dentistry, 27, 1999, pp. 465-477.

Darvell, B.W and Dyson, J.E., "Testing Machine for Dental Air-turbine Handpiece characteristics: Free-running speed, Stall torque, Bearing resistance," Operative Dentistry, 30-1, 2005, pp. 26-31.

Monaghan, D.M., Wilson, N.H.F, and Darvell, B.W., "The Performance of Air-turbine Handpieces in General Dental Practice," Operative Dentistry, 30-1, 2005, pp. 16-25.

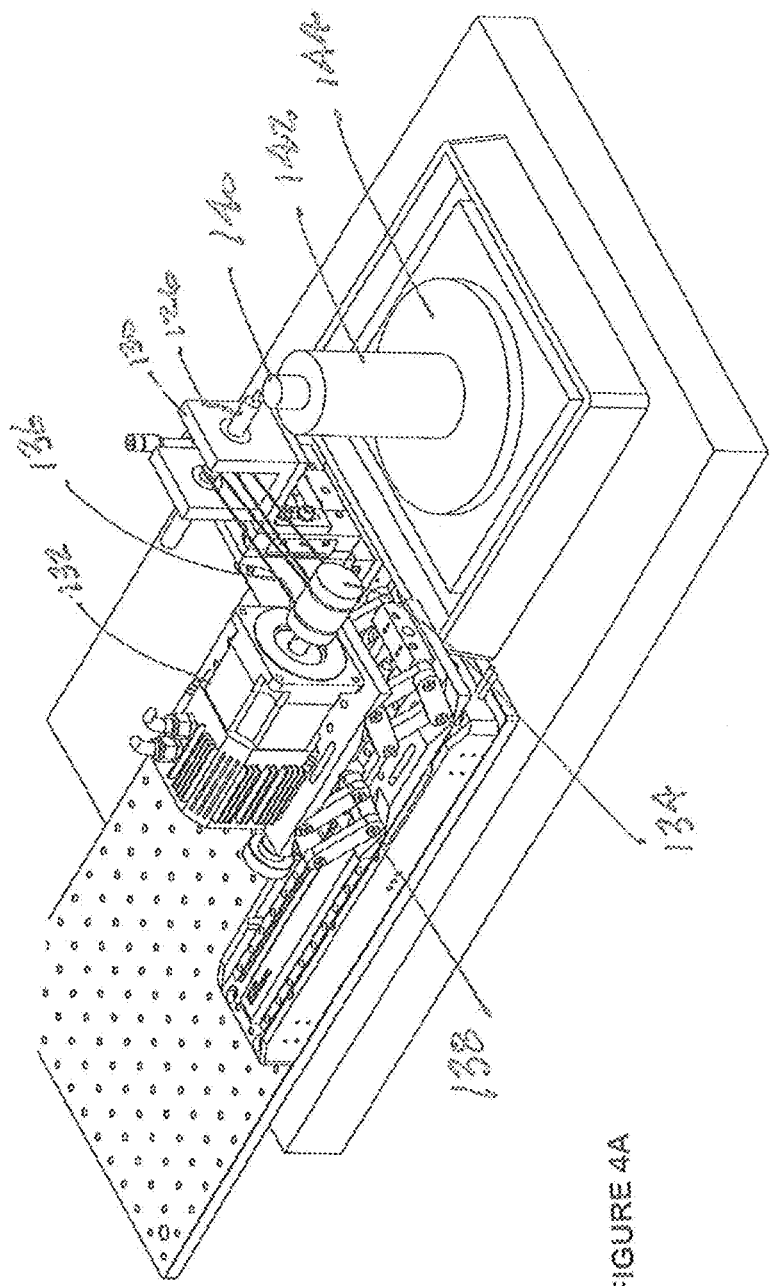

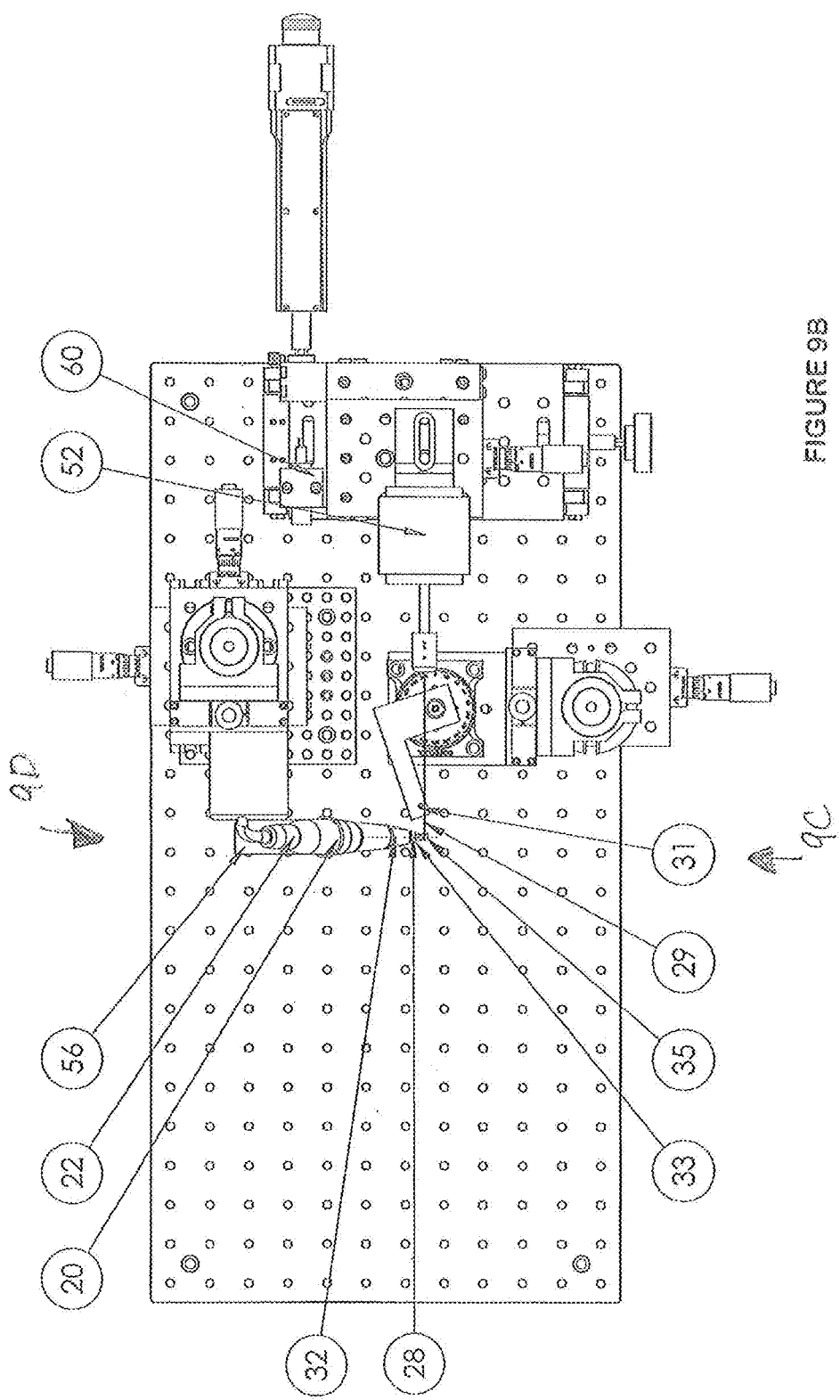

METHOD AND APPARATUS FOR CHARACTERIZING HANDPIECES

CROSS REFERENCE TO RELATED APPLICATION

This is a utility application related to and incorporating by reference previously filed provisional application Ser. No. 61/790,395 entitled "Method and Apparatus for Characterizing Handpieces" in the U.S. filed on Mar. 15, 2013.

BACKGROUND OF THE INVENTION

In a principal aspect the present invention comprises a system for measurement of various output operating parameters of fluid or air driven, rotary shaft tools such as dental handpieces, polishing devices, drills and the like. Parameters such as dynamic torque, stall torque, tool speed, tool efficiency, air or fluid consumption and other aspects of tool operation provide important information regarding tool design. That is, development of comparative data relating to the operating characteristics of such tools facilitates development of improved tool designs. Further, such information may assist in development of engineering and operational standards that relate to tool use and safety.

Thus, it is an object, aspect and feature of the present invention to provide a system whereby air or fluid driven tools may be operated in a manner which enables ascertainment of operational parameters relating to such tools based on the fluid or air supply provided to such tools, the loads acting on the tools and the component parts of the tools, and environmental factors such as temperature and density of the fluids or air composition utilized to operate the tool.

Another aspect, feature and object of the invention is to provide a means by which air and fluid driven tools may be compared or tested for efficiency and consistency of operation.

Yet another object, advantage, feature and aspect of the present invention is to provide a systematic protocol for the evaluation of air or fluid driven tools of various makes, sizes and designs.

A further object, advantage, aspect and feature of the invention is to provide testing protocols that are consistent and can be consistently applied and utilized with respect to design, testing and otherwise evaluating such tools.

These and other objects, advantages and features of the invention will be set forth in the following specification.

SUMMARY OF THE INVENTION

Briefly, the present invention comprises a tool testing assembly for an air or gas driven tool which incorporates sensors for measurement of various parameters associated with the operation of the tool. The assembly includes, among other features, a mount or support stand for maintaining the tool in a fixed position with respect to an air or fluid supply and power inlet subassembly. Fluid, input sensors are provided for control and sensing fluid flow, fluid pressure, fluid temperature and other parameters associated with pressurized operating fluid provided to the tool mounted on the mount. Further, the testing assembly includes a unique mandrel which may be inserted into the mechanical output drive of the tool mounted on the tool mount. Force sensors are arranged to engage a cord fitted over or attached to the mandrel and additional sensors measure mandrel movement, temperature and other aspects of operation of the mandrel. Thus the tool and, more particularly, the effect of load and other aspects of operational use of the tool are detected, recorded, stored and processed. Thus, the assembly includes data collection, processing and storage devices for collecting and processing the sensor data associated with fluid provided to drive the tool as well as tool output sensed by monitoring the mandrel. The separate sensors enable determination energy input to the tool and work or operational output of the tool as well as other operational characteristics of the tool.

The assembly or apparatus is therefore capable of testing multiple performance characteristics associated with the tool. Test methods and protocols are disclosed utilizing the test assembly to determine factors including, by way of example, air or fluid supply associated with the input to the tool, torque and bearing resistance associated with the operation of the tool and by the component parts of the tool, free running speed and the degree of fluid consumption by the tool and other aspects of the utilization of supply air or fluid to operate the tool as affected by loads on the tool.

In an embodiment of the invention, the tool is mounted on an adjustable stand in a fixed position. A compressed air or fluid supply is provided to the tool via an air inlet tube or similar source through a pressure regulator. Various sensors are attached to the air or fluid tube intermediate the pressure regulator and a fluid inlet coupler to the tool. A first pressure sensor is provided downstream from the pressure regulator. A mass flow meter is positioned downstream from the first pressure sensor. A second pressure sensor is maintained downstream from the mass flow meter. A temperature sensor is provided and a third pressure sensor are provided adjacent the fluid inlet to the air tool.

The fluid driven tool typically includes a rotary driven output shaft removably mounted in a collet. The shaft typically is designed to thereby comprise a tool element such as a burr, polishing pad, drill or the like. A special test mandrel in accord with the invention may be substituted or inserted in the tool collet or connected to the output drive shaft of the tool. The mandrel is designed to receive an elongate thread or cord or analogous flexible line wrapped around a generally cylindrical end surface of the mandrel. The opposite ends of the line extend from the mandrel typically directed in opposite directions from the center line axis of the mandrel and are connected respectively to a first force sensor and a second force sensor positioned respectively on opposite sides of the mandrel. However, other arrangements of the force sensors may be adopted. The force sensors are each mounted on a platform which may be adjusted to provide tension on an end of the cord or thread attached to the force sensor. The force sensors thus, in combination, supply a measured tensile force on the cord which is wrapped around the mandrel. The force may be adjusted by control of the adjustable platforms on which the force sensors are mounted.

A speed sensor is provided to measure the rotational speed of the mandrel in response to air flow and pressure. A temperature sensor may be positioned to sense the temperature of the mandrel cylindrical surface.

Data collected from the various sensors may be evaluated to determine aspects of tool operation such as and including torque, stall torque, bearing resistance of the tool, comparative speed versus torque data, comparative power versus speed data, efficiency of the tool relative to fluid consumption, pressure response, and dynamic torque testing over a range of speeds and relative to power.

In an embodiment, the mandrel may provide for attachment of one end of the cord or string directly to the mandrel. Multiple wrappings of the cord about the mandrel and attachment of the free end of the cord to a single force sensor will enable measurement of other operational features of the tool as described herein such as stall torque and related features. Thus, with respect to stall torque associated with the tool under consideration, minimum and maximum torque measurements may be derived including instantaneous stall torque, average stall torque, maximum stall torque, minimum stall torque, bearing resistance torque at various pressures with and without loads. These features, among others, are discussed hereinafter in greater detail.

BRIEF DESCRIPTION OF THE DRAWING

In the detailed description which follows, reference will be made to the drawing comprised of the following figures:

FIG. 4A is an isometric view of an embodiment of apparatus for polishing the mandrel of FIGS. 2-4;

FIG. 9B is a top plan view of the embodiment configuration of FIG. 9A;

DESCRIPTION OF EMBODIMENTS OF THE INVENTION

Figure 1:
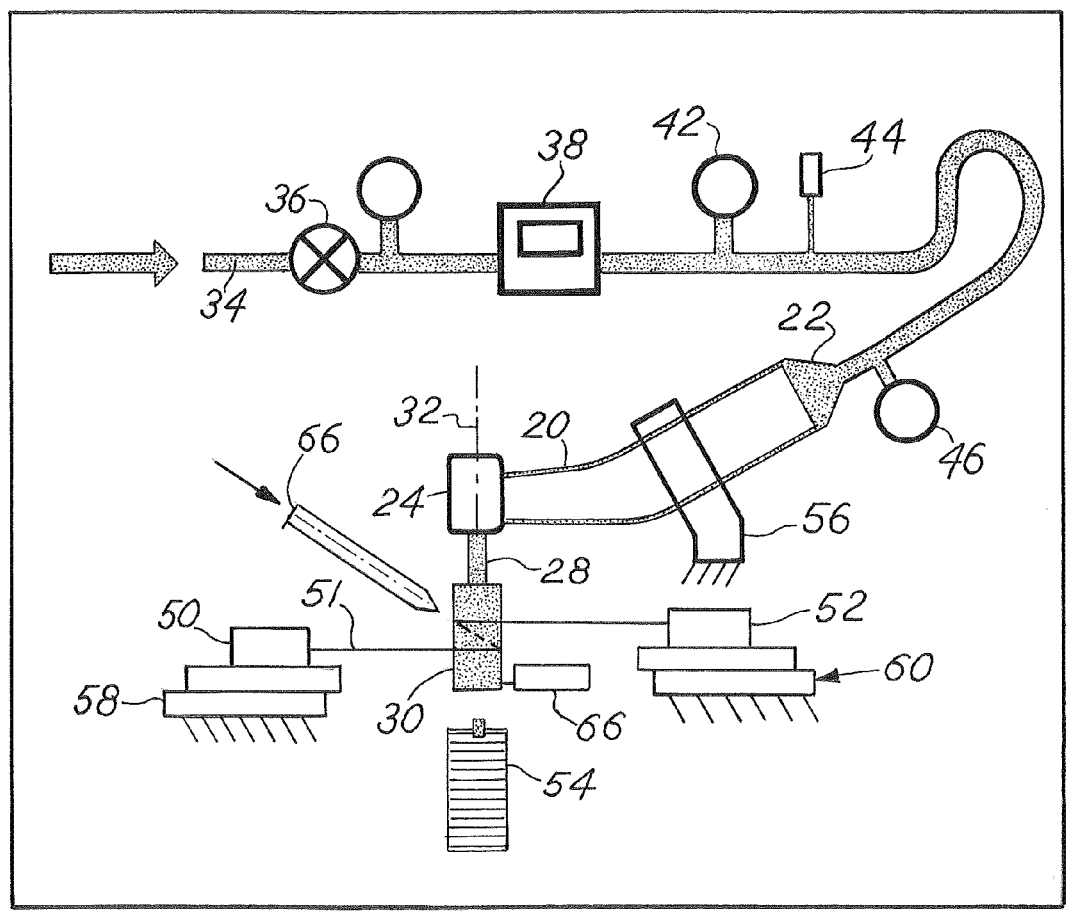
FIG. 1 is a diagrammatic illustration of a testing apparatus configuration used to control and monitor air pressure and flow as well as provide multiple tool output sensors that source data for processing, storage and evaluation.
Figure 1A:
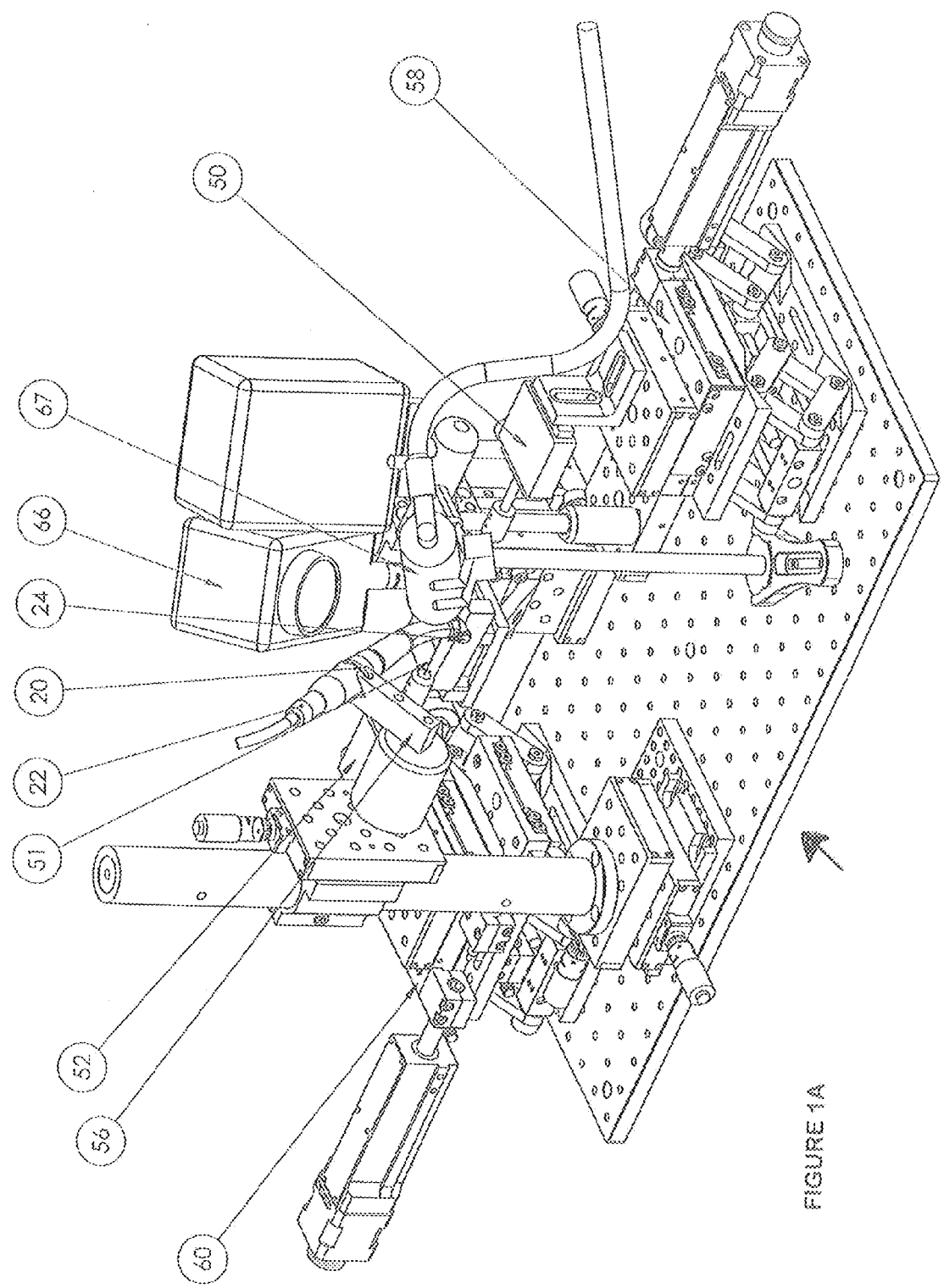
FIG. 1A is an isometric view of an embodiment of the apparatus in accord with the illustration of FIG. 1.
Figure 1B:
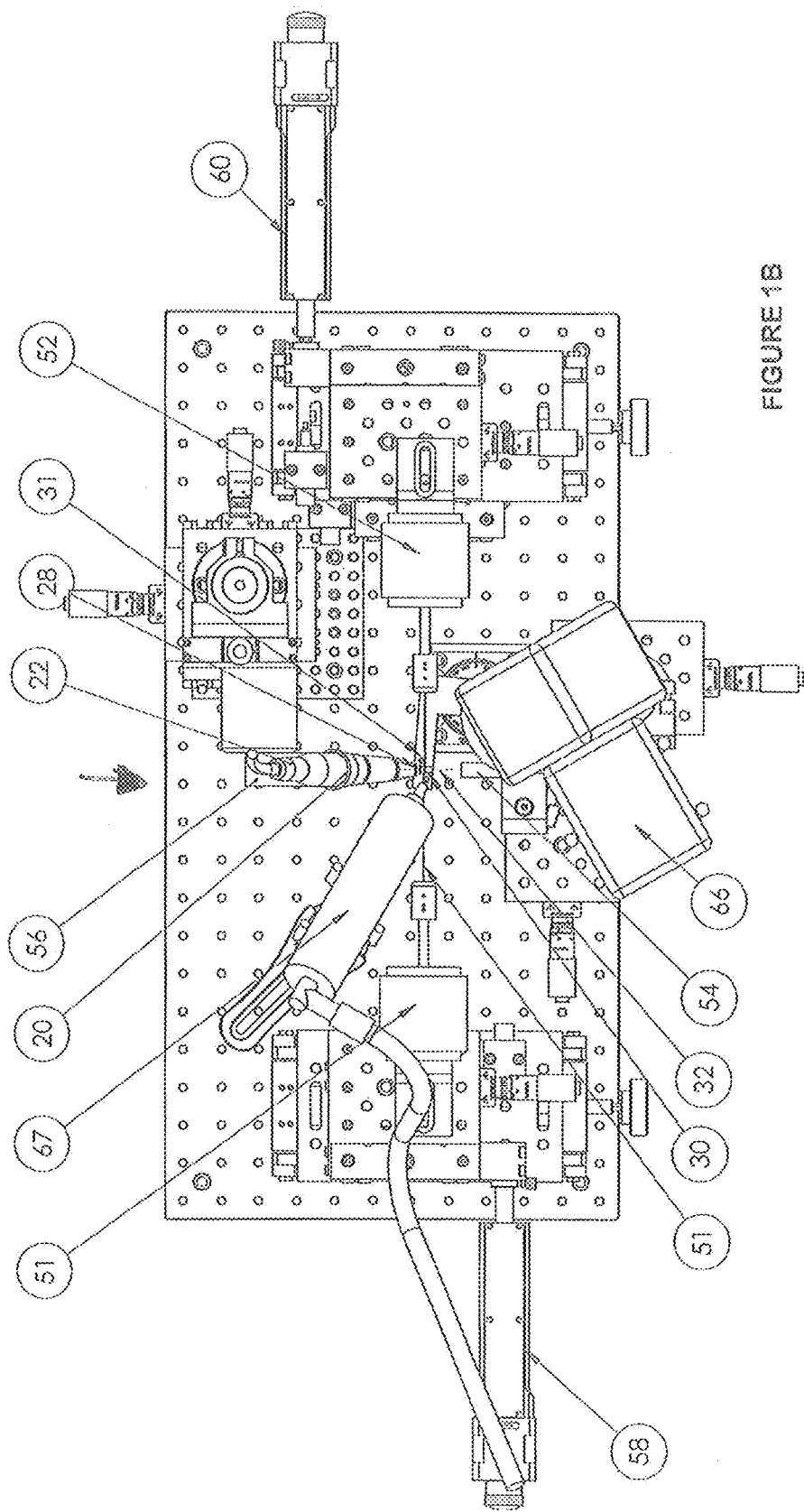
FIG. 1B is a top plan view of the embodiment of FIG. 1A.
Figure 1C:
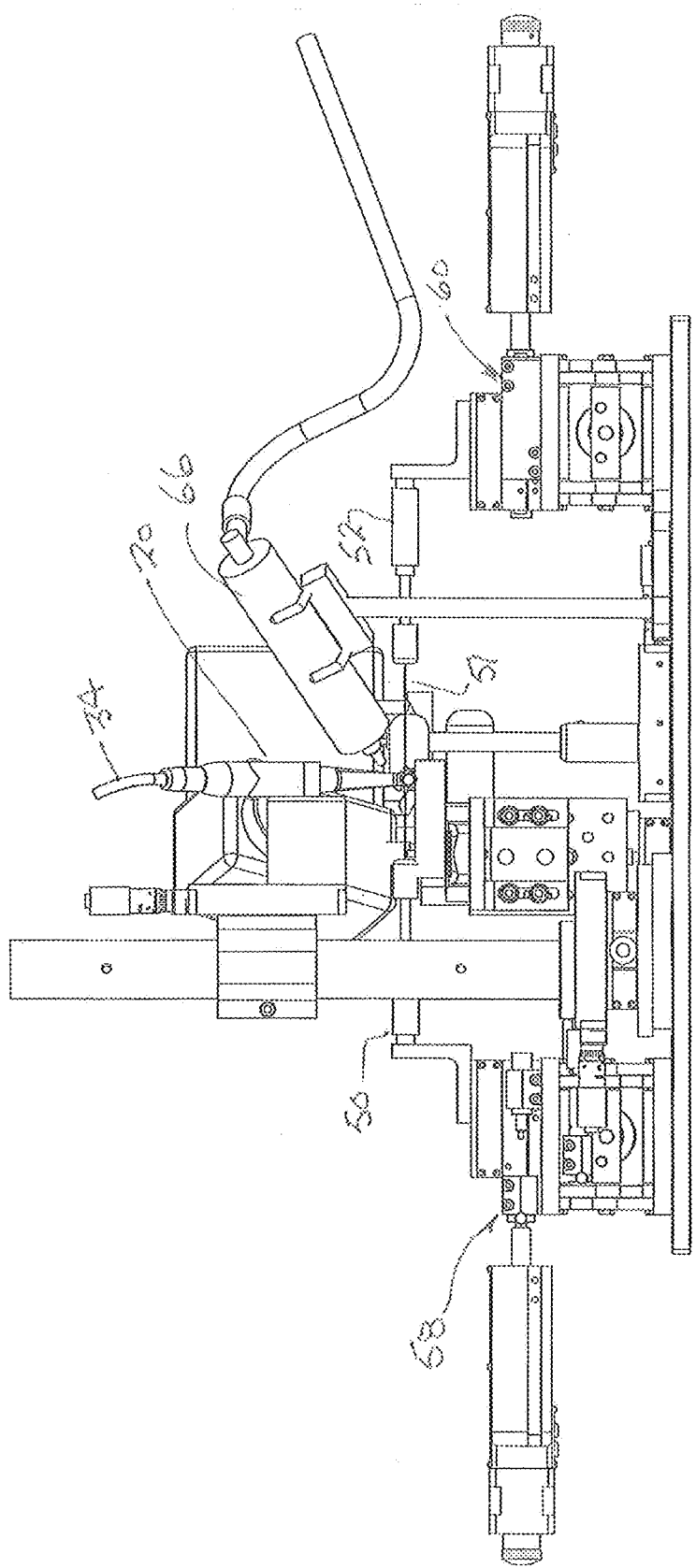
FIG. 1C is a side plan view of the embodiment of FIG. 1A viewed in the direction of the arrow in FIG. 1A and FIG. 1B.
Figure 2:
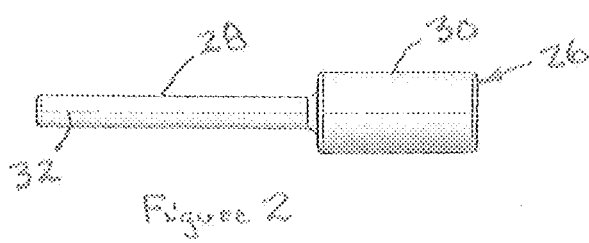
FIG. 2 is a side elevation of a typical mandrel useful in the practice of the invention.

FIG. 1 pictorially illustrates testing apparatus capable of characterizing a dental handpiece, by way of example. FIGS. 1A, 1B and 1C depict views of an embodiment of the apparatus in accord with FIG. 1. Referring to those Figures, a dental handpiece or air driven tool 20 includes a fluid inlet 22 and typically a turbine type motor (not shown) incorporated in a housing 24. A mandrel 26, described in greater detail hereinafter, includes a shaft 28 fitted into the housing 24 to engage a collet or other output mechanism of a drive turbine or similar prime mover. The mandrel 26 further includes a cylindrical body 30 coaxial with the shaft 28. Rotation thus is effected around a longitudinal axis 32. The turbine within the tool 20 is driven by fluid provided through the inlet 22 and exhausted from an exhaust port downstream from a turbine assembly within the housing 24 which rotates the shaft 28 of mandrel 26 inserted and locked in a collet of tool 20.

The fluid supply to the tool 20, by way of example, is a compressed air supply introduced through the tube 34. A pressure regulator 36 is provided to control the inlet pressure through the tube 34. A first pressure sensor 38 provides data to a recording computer (not shown). Similarly, a downstream mass flow meter 40 in the fluid supply line 34 provides data to the computer processing and storage assembly. A second pressure sensor 42 is provided downstream from the mass flow meter 40. A temperature sensor 44 is also provided to measure the temperature of the drive fluid in the line 34. A third pressure sensor 46 is provided at or near the inlet 22. Data from all of the input and output sensors is routinely collected and stored for analysis.

Associated with the output of the tool 20, and, more particularly, with the operation of the mandrel 26 which is rotated by the tool 20 driving the shaft 28, are a first force sensor 50 positioned on one side of the mandrel 26 and a second force sensor 52 positioned on the opposite side. A thread, suture or cord 51, typically of silk, is wound around the mandrel body 30 and connects at its opposite ends respectively to the first force sensor 50 and second force sensor 52. A speed sensor 54 is provided to measure the rotational speed of the mandrel 30. All of the sensors provide data input to the computer assembly for processing, storage and recordal. The data may thus be assimilated in manners known to those of skill in the art to provide calculated relationships between the various inputs and outputs of the tool 20.

Thus, there is an input of various test parameters and a subsequent output of test data associated with the operation of the mandrel. Typically, the following performance characteristics can be measured: rotational speed; namely, the free running speed as well as the free running rotational speed versus supply pressure, dynamic torque (torque versus speed), stall torque, tool bearing resistance, power generation (power versus torque and power versus speed) and efficiency.

Typically the mandrel 26 is made from tungsten carbide or materials having similar characteristics of hardness, heat resistance, heat conductivity and a capability to provide a low friction surface. The mandrel 26 includes body 30 of a given or measured constant radius and shaft 28 which may be fitted into the handpiece 20 that is being tested.

Figure 4:
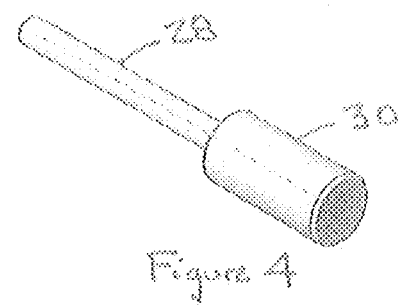
FIG. 4 is an isometric view of the mandrel of FIG. 2.
Figure 3:
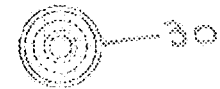
FIG. 3 is an end view of the mandrel of FIG. 2.
Figure 4B:
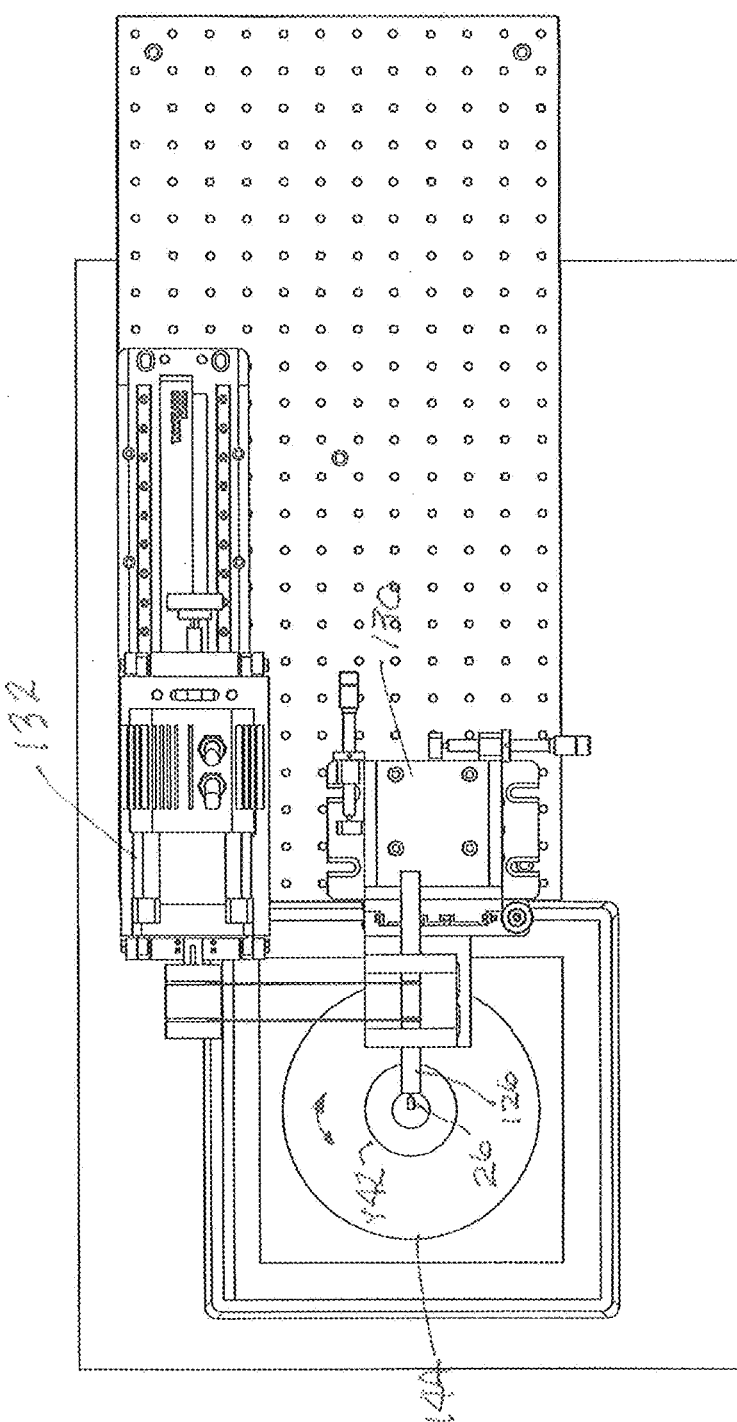
FIG. 4B is a top plan view of the polishing apparatus of FIG. 4A.
Figure 4C:
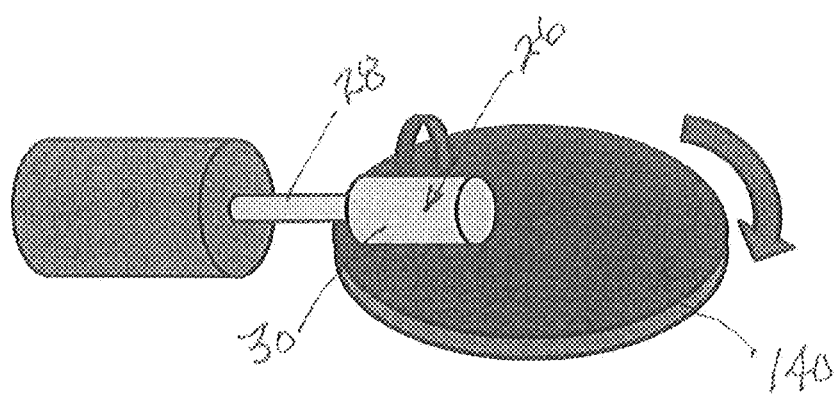
FIG. 4C is a diagrammatic illustration of the polishing protocol utilized to prepare a mandrel of the type depicted in FIGS. 2-4 utilizing the apparatus of FIGS. 4A and 4B.

FIGS. 4A, 4B and 4C depict in greater detail the use of the mandrel 26 as well as the manner of conditioning the mandrel and preparing the mandrel for use in combination with the embodiment depicted in FIGS. 1, 1A, 1B and 1C. Thus, the mandrel body 30, which is coaxial with the shaft 28, is prepared by polishing the surface of the body 30. The surface of the body is the outside surface of the cylinder of body 30. The mandrel 26 is manufactured, for example, from a sintered carbide stock.

As cast or molds are otherwise formed, the mandrel 26 will contain various surface defects observable under a microscope. Thus, as a first step in the preparation of the mandrel 26 the approximate size of the diamond particulates of the polishing mixture for the mandrel surface is determined. Typically, the polishing mixture is in the form of a mix of a spray and paste material. As shown in FIG. 4C, the mandrel 26 and more particularly the surface of the body 30 is rotated or polished to achieve a smooth, uniform finish on the entire circumference of the body 30 by placing the surface of the body 30 against a brake drum of a polishing apparatus as depicted in FIGS. 4A and 4B. The mandrel is rinsed and cleaned after each polishing step and multiple steps are typically necessary. After each polishing step, the mandrel is examined with a microscope to ensure that the surface scratches are from the previous polishing step and have been created by that polishing step. With each step in the polishing sequence, grit size is decreased and typically the mandrel 26 is moved to the opposite side of a platen or polishing surface so that the striations from polishing will be oriented opposite to those of the previous polishing step. This permits visual examination to determine the polishing step is completed. Typical gilt progression in the polishing mix will be as follows: 15 µm, 9 µm, 3 µm, 1 µm, and a grit less than 0.3 µm. It has been found that the sintered carbide stock is of such a nature that effective polishing below 0.3 µm is not practical.

Referring now to FIGS. 4A and 4B, the mandrel 26 is mounted in a mandrel collet 126 rotationally mounted in a chuck stand or mandrel collet stand 130. A motor 132 with a rotary output shaft 134 is connected by belts or loops 136 to the chuck or collet shaft or mount 126. The motor is mounted on a stand 138 which is adjusted to appropriately engage the belts 136 and maintain the belts 136 to operationally drive and rotate the collet 126 and simultaneously the mandrel 26 mounted in the collet 126. The stand 138 may move reciprocally, but typically is locked in position when driving the belts 136. The chuck or collet stand 130 is also adjusted to an appropriate position to engage the body 30 of the mandrel 26 with a polishing surface 140 coaxially mounted in a support post 142 of a rotational drive platen 144. The motor 132 as well as the shaft 142 are capable of being driven in either rotational sense. As previously mentioned, the protocol for polishing the outer surface of the body 30 is facilitated if the rotational direction of the mandrel 26 and/or the polishing surface 140 are reversed between each step of the polishing sequence. Once the mandrel 26 is adequately polished, the mandrel is inserted into the handpiece 20. Thus, and subsequently, the handpiece is fixed upon a mount 56.

In operation, the handpiece 20 is fixed upon a mount 56 and is substantially not moveable during operation. Mount 56 is typically adjustable. Silk cord 51 or other thread, ribbon, tape, string, wire or the like having similar characteristics of strength and heat resistance and ability to provide a low friction surface is then wrapped around the body 30 of mandrel 26. The cord 51 is aligned with appropriate bearing guides such as guide 31 in FIG. 9 positioned intermediate the mandrel body 30 and a force sensor 50 or 52. The cord or thread 51 thus is attached at each end to a force sensor 50, 52 on mounts 58, 60 adapted to receive the thread 51 and keep the thread 51 in alignment. The force on the thread 51 is controlled through the force 50, 52 sensors mounted on the two computer driven, linear stages or mounts 58, 60. An optical infrared tachometer or speed sensor 54 is used to measure the rotational speed of the mandrel body 30. Data from the sensors for force 50, 52, speed 54 and air pressure 38, 42, 46 are acquired with an analog to digital control board connected to the computer assembly. A software program monitors and records the data which is then analyzed using further software designed to provide the comparison and data analysis associated with the input data.

FIGS. 2, 3, 4, 4A, 4B and 4C illustrate a typical mandrel and construction of the mandrel associated with the practice of an embodiment of the invention. Thus, mandrel 26 includes an elongate shaft 28 with axis 32 and coaxial body 30. The mandrel body 30 includes a constant diameter along its axial length and is designed for receipt of a cord 51 as previously described. The shaft 28 is designed to fit into the collet of tool 20 which is being evaluated, for example, with respect to a dental tool with chuck or collet which retains a polishing pad or the like.

Figure 9:
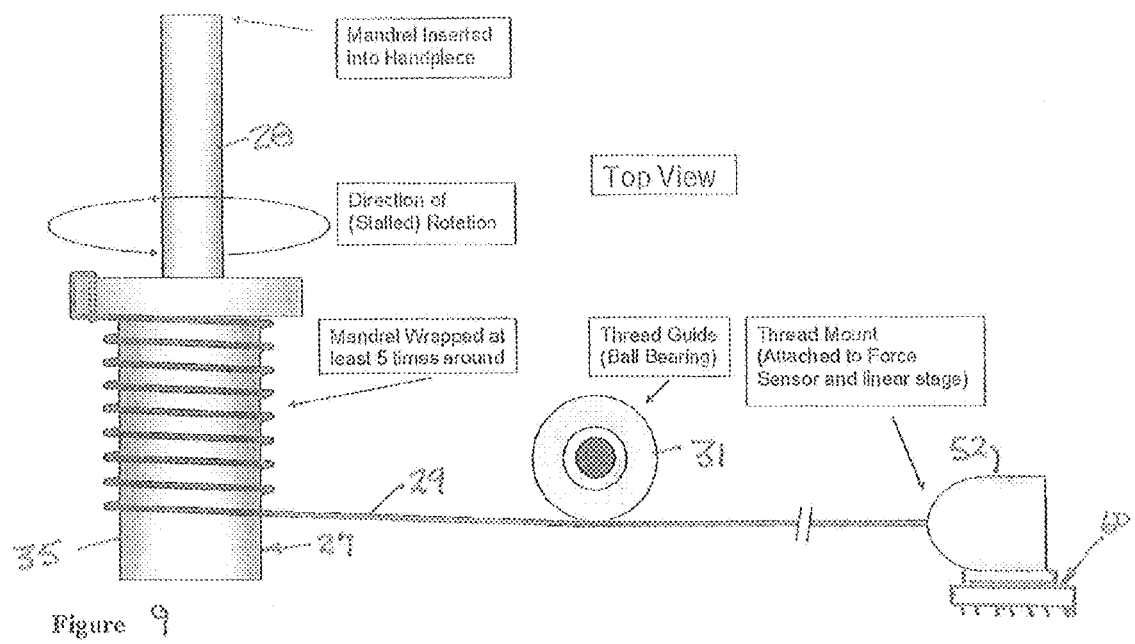
FIG. 9 is a diagrammatic illustration of a mandrel set up to measure stall torque and bearing resistance.
Figure 9A:
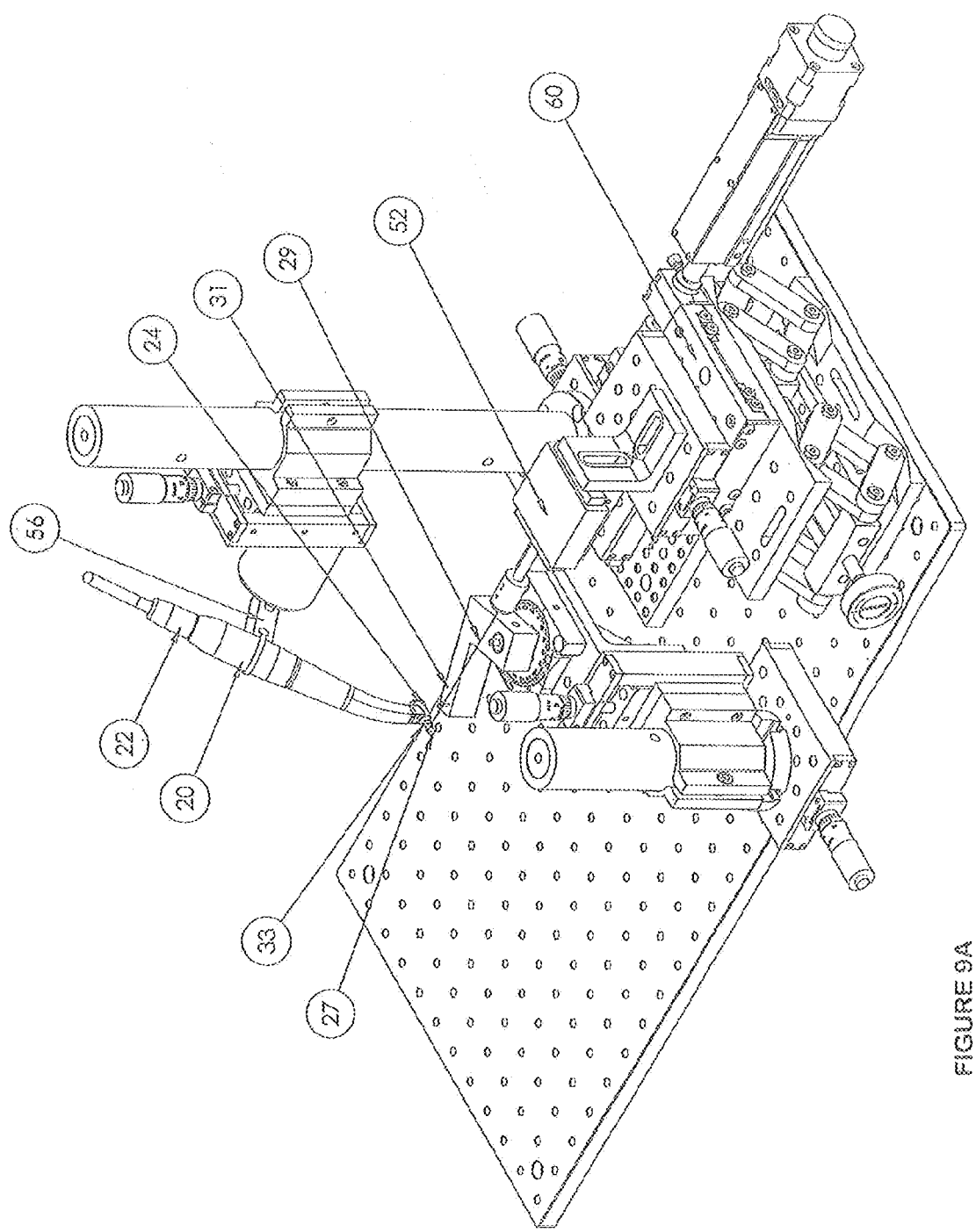
FIG. 9A is an isometric view of the embodiment of FIG. 1A configured in accord with a set-up as illustrated in FIG. 9 for determination of certain torque measurements.
Figure 9C:
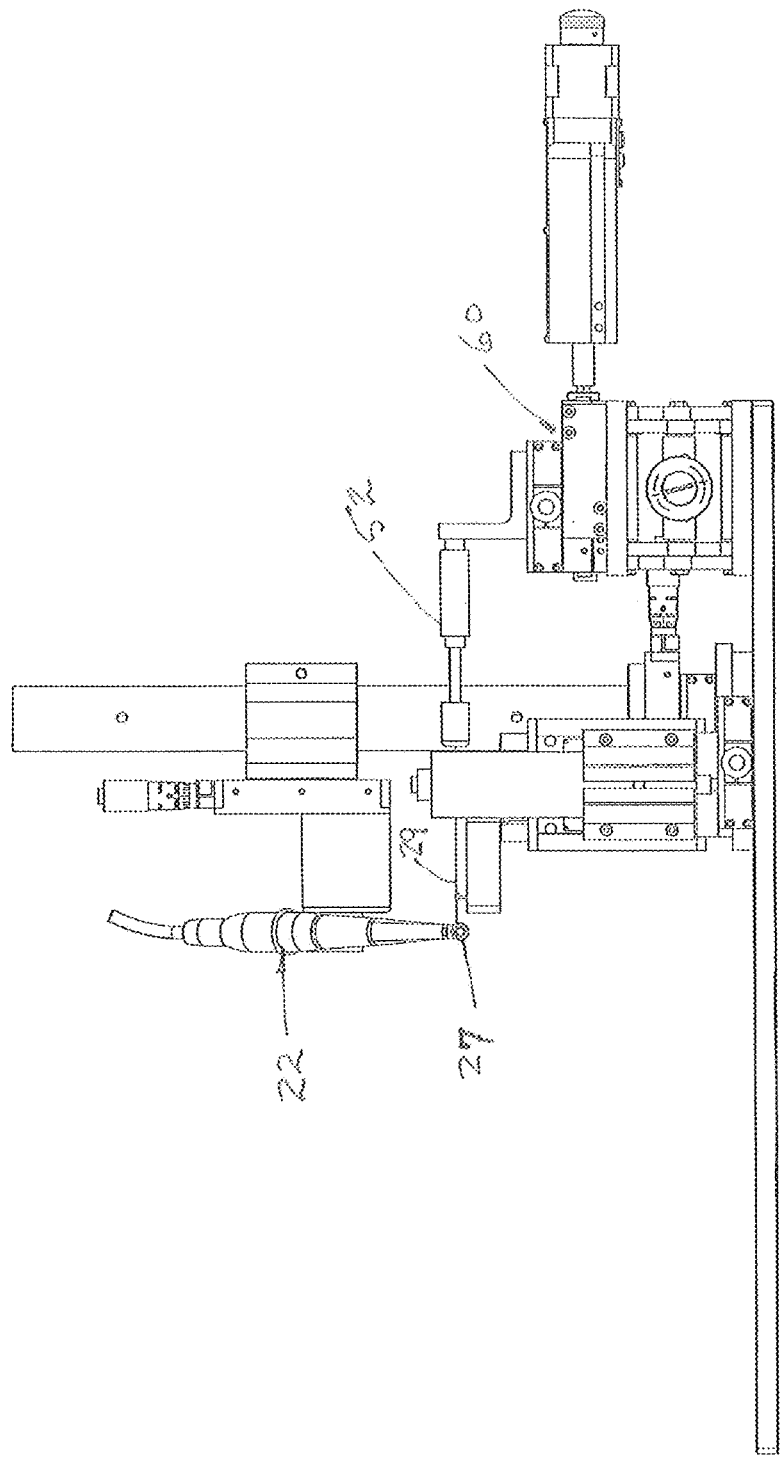
FIG. 9C is a side plan view of the embodiment configuration of FIG. 9B in the direction of the labeled arrow, 9A.
Figure 9D:
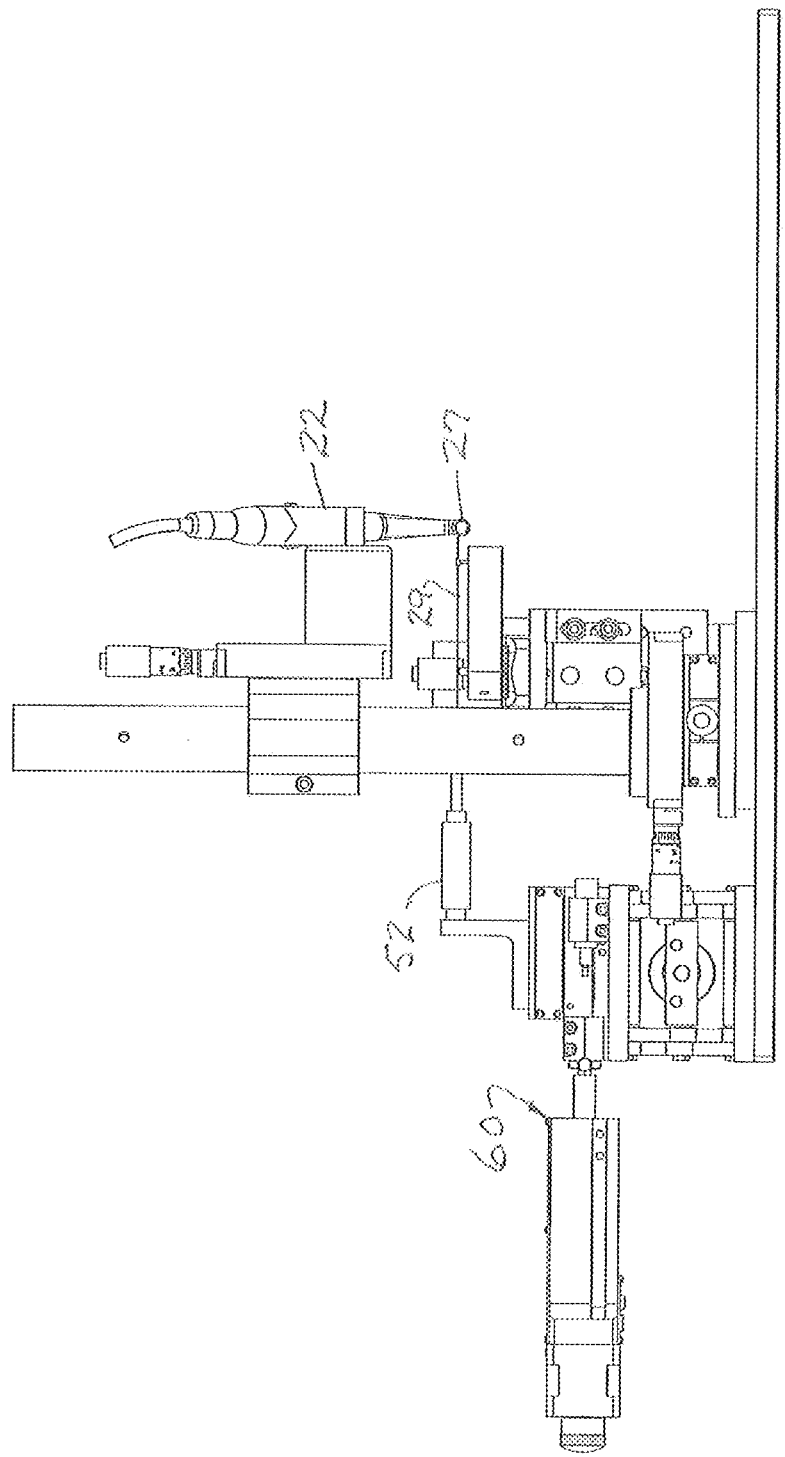
FIG. 9D is a side plan view of the embodiment configuration of FIG. 9A in the direction of the labeled arrow 9D.

FIG. 9 illustrates an alternate mandrel construction wherein the alternative mandrel 27 includes a circumferential flange or collar 33 designed for use with respect to determination of stall torque. In such a circumstance, a cord 29 is wrapped multiple times around the cylindrical body 35 of the mandrel 27 with one end of the cord 29 affixed to the flange 33. The direction of rotation of the shaft 28 is depicted by the arrow. The opposite end of cord 29 is attached to a force sensor 52 or mount 60 which is adjustable and may provide increasing force or pull on cord 29. The force sensor 52 on mount 60 provides a force which ultimately will cause the rotation of the mandrel to terminate, thus giving input data with respect to the amount of force necessary to stall the operation of the tool.

FIGS. 9A, 9B, 9C and 9D illustrate the set-up of the embodiment of the invention for the purpose of measuring stall torque. The tool 20 is mounted on a shaft or support 28 and adjusted in the manner depicted with the attachment of one end of cord 29 to the mandrel 27 as depicted in FIG. 9. In effect, the second force sensor 50 is eliminated from the embodiment depicted in FIG. 1A and the remaining component parts of the system of FIG. 1A are thus illustrated in FIGS. 9A, 9B, 9C and 9D along with the schematic view and in the manner depicted in FIG. 9 of attachment of the cord 29 to the body of the mandrel 27.

The apparatus utilizing either mandrel 26, 27 is capable of testing a number of performance characteristics. Certain examples are set forth hereinafter. Additional tests and comparisons can be easily developed by minor configuration of the testing apparatus and the data which is secured therefrom. Set forth hereinafter are three testing method examples utilizing the apparatus. The air supply configuration described with respect to FIG. 1 is substantially the same for each of the three examples.

Figure 11:
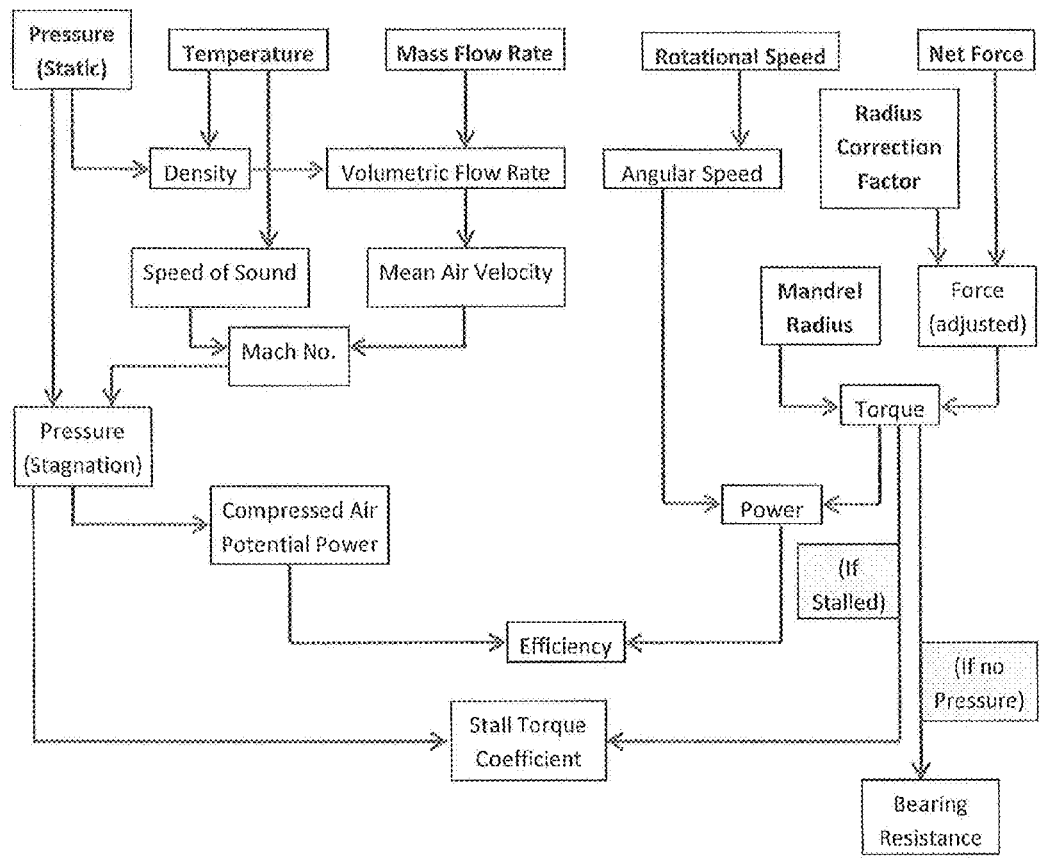
FIG. 11 is a flow chart of the data analysis methodology associated with the testing apparatus of the invention. The analysis is performed on various data processing scripts written in Visual Basic for use with the National Instruments DIAdem software environment which will parse, organize and analyze the data. This methodology is applied to dynamic torque, stall torque and bearing resistance with associated scripts. Each value is calculated for all time points in the data set and minimum, maximum and average values are extracted.

Data analysis is performed with various data processing scripts written in Visual Basic for use with the National Instruments DIAdem software environment. This system will parse, organize and analyze the data in accord with various flow charts set forth herein. This general methodology is applied to the determination of dynamic torque, stall torque and bearing resistance. Each value is calculated for all time points in the data set and minimum, maximum and average values are extracted. FIG. 11 is a flow chart which depicts this general methodology and the data factors that are collected.

EXAMPLE 1

Supply Air Measurement and Control

A clean compressed air source inputs into a pressure regulator, which can be used to control the air supplied through the system to the handpiece. Pressure sensors at three locations, as disclosed in FIG. 1 for the air supply, measure the pressure at key points in the apparatus: the pressure regulator, the equivalent of what would be, e.g., the "dental unit" used by a practitioner, and, in this example, at the end 72 of six feet of standard dental tubing where the air is supplied directly to the handpiece. Mass flow meter 40 between the first and second pressure sensors 38, 42, allowing for continuous monitoring of the flow rate through the apparatus. Thermocouples 44 placed at the junctions of the second and third pressure sensors 42, 46 provide temperature measurements which can be used for calculating parameters of the gas flow, as well as establishing when a steady state condition to reduce variability has been achieved.

The handpiece 20 to be tested is fixed on the apparatus by an adjustable gripping device 56. Manual linear stages of mount 56 allow for each major component of the apparatus (force sensor and motorized stage units, adjustable gripping device, speed sensor, and alignment bearing system) to be precisely aligned horizontally and vertically so as to ensure measurement accuracy.

The apparatus can be configured for one of three testing methods: (1) method to test dynamic torque; (2) method to test stall torque and bearing resistance; and (3) method to test free running speed and supply air.

1. Dynamic Torque. Silk thread 51 or the like is wrapped around test mandrel body 30 of known radius and the ends of the thread are attached to force sensors, as shown in FIG. 1. The measured force and known radius allow the calculation of torque while a non-contact tachometer 54 is used to measure the speed of rotation. The apparatus is able to acquire data at a high resolution with the dental air turbine handpiece operating at high powers. Important components of the apparatus in the configuration are the following:

a. Mandrels. Test mandrels having specific properties, i.e., sufficient hardness, heat resistance, heat conductivity, and ability to provide a low friction surface (FIGS. 2-4) are an important component of this testing system. The mechanical braking system of the apparatus generates heat as it dissipates energy from an air turbine handpiece that is tested. Therefore, a smooth surface and a high tolerance for heat and wear are important factors in mandrel design.

b. Cooling air jet. A cooling device in an embodiment such as a Vortex Tube 66 is used to produce a jet of cooling air aimed directly at the principal point of heat generation and thread damage: the mandrel/thread interface site. When aligned correctly, this jet 66 produces a significant increase in heat dissipation while producing a negligibly small force on the braking system. This allows successful, sustained testing over twenty watts without burning or depositing thread material on the mandrel.

c. Infrared thermal imaging and adjustable stage movement parameters. Including infrared thermal imaging device 66 in FIG. 1 enables real time monitoring of the temperature of the braking system, but this feature is not necessarily a required element. This allows tests to be aborted or testing parameters such as stage movement speed to be altered to avoid burning and melting of the thread 51 and the generation of unreliable data.

d. Data analysis. Software programs adapted to calculate additional parameters of handpiece function from the acquired data, such as power in watts, and can compare these at each individual data acquisition time-point. FIGS. 5-8 illustrate data collected utilizing the described arrangement.

Figure 5:
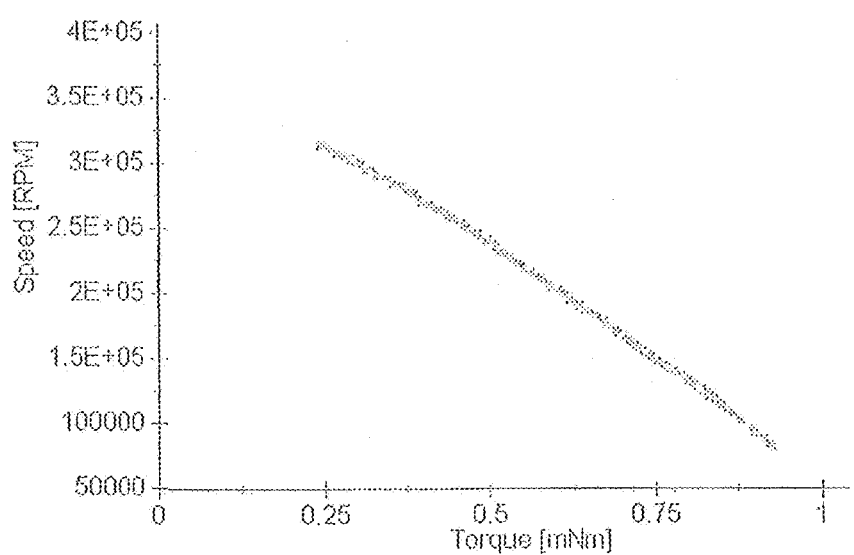
FIG. 5 is an example of a speed versus torque plot for an air turban handpiece.

FIG 5 compares sample speed versus the torque curve for a handpiece.

Figure 6:
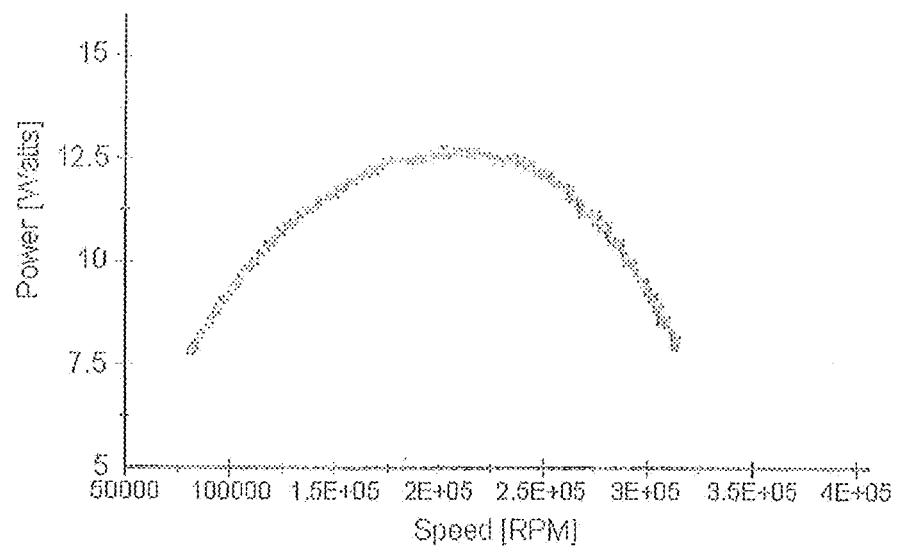
FIG. 6 is a sample power versus speed plot for a typical dental air turbine handpiece.
Figure 7:
FIG. 7 is a sample efficiency plot ftor a dental air turbine handpiece.

FIG 6 is a sample of a power associated with the tool versus the speed of operation of the tool in revolutions per minute of the mandrel. A related graph is depicted in FIG. 8 which shows the efficiency of a typical tool.

Figure 8:
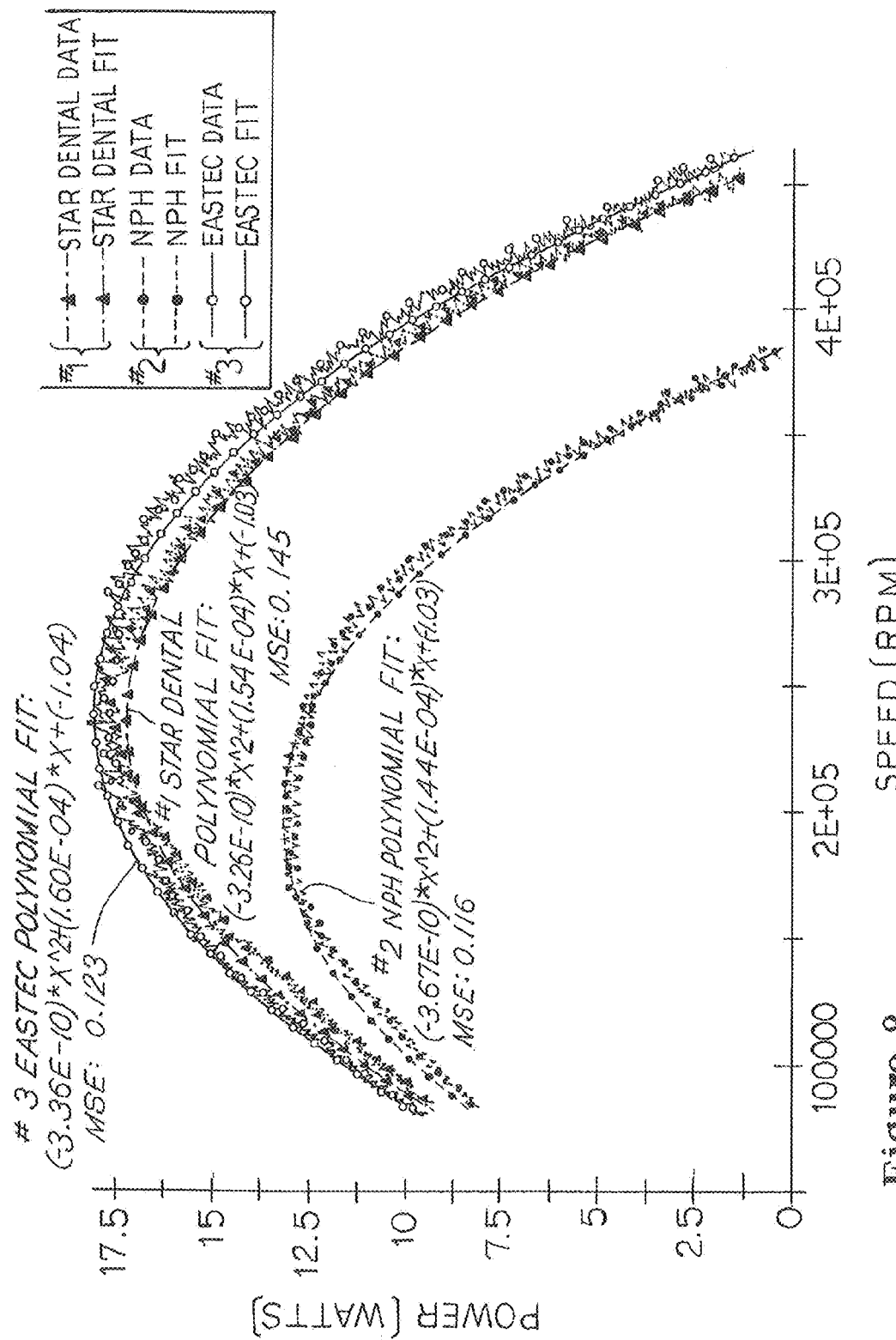
FIG. 8 is an example of multiple dynamic torque testing data comparison curves of three different types or makes of dental air turbine handpieces.

FIG 8 is a chart illustrating the comparison of multiple air turbine handpieces. The speed versus the power is analogous to the curve depicted in FIG. 7. Thus, it can be seen that various tools may be compared one to the other to determine which designs provide the most effective power output with respect to speed.

Figure 12A:
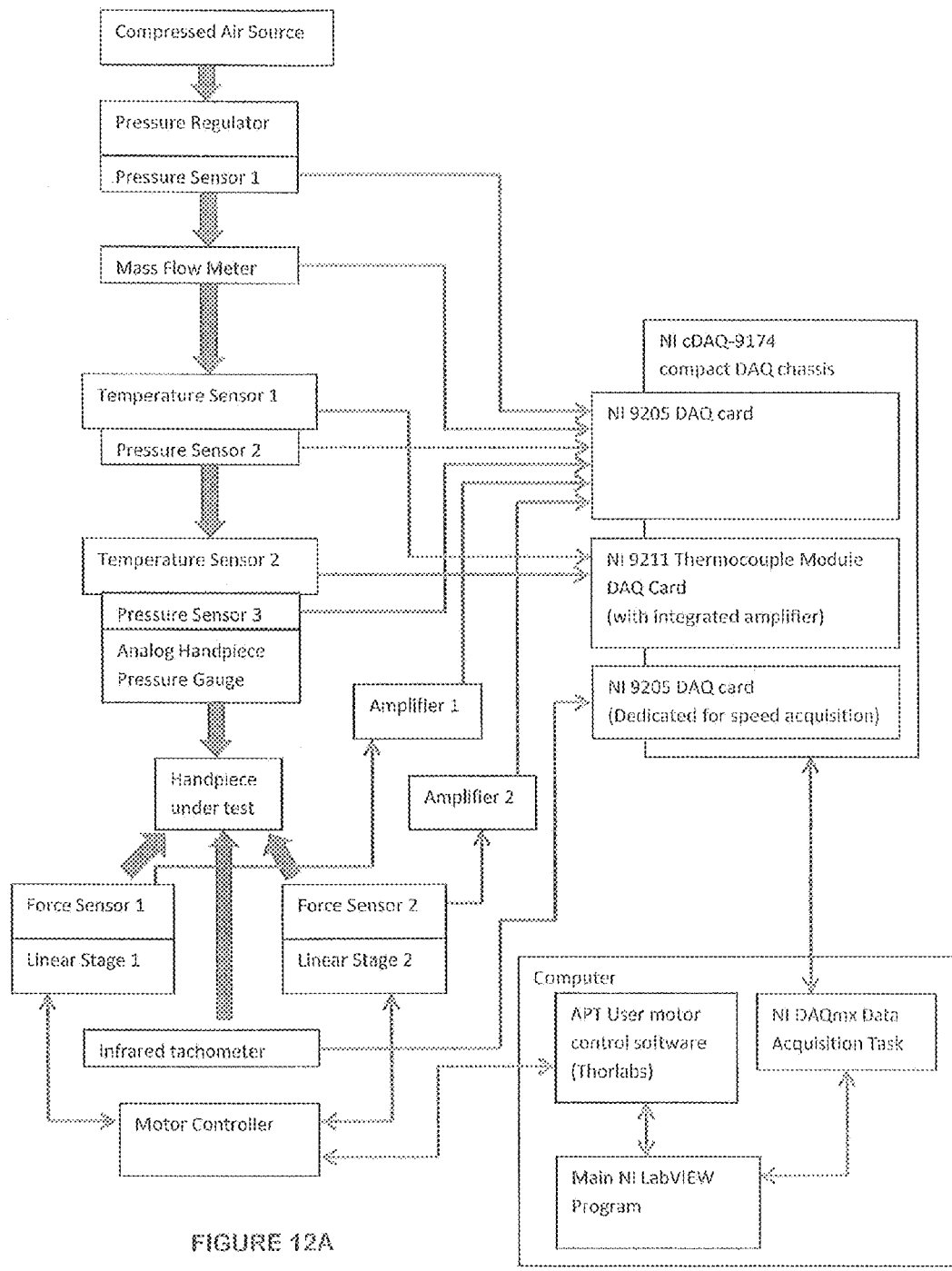
FIG. 12A is a flow chart setting forth the data acquisition flow diagram for conducting a test with respect to dynamic torque including securing data input, recordal of all input and output and processing of the data.
Figure 12B:
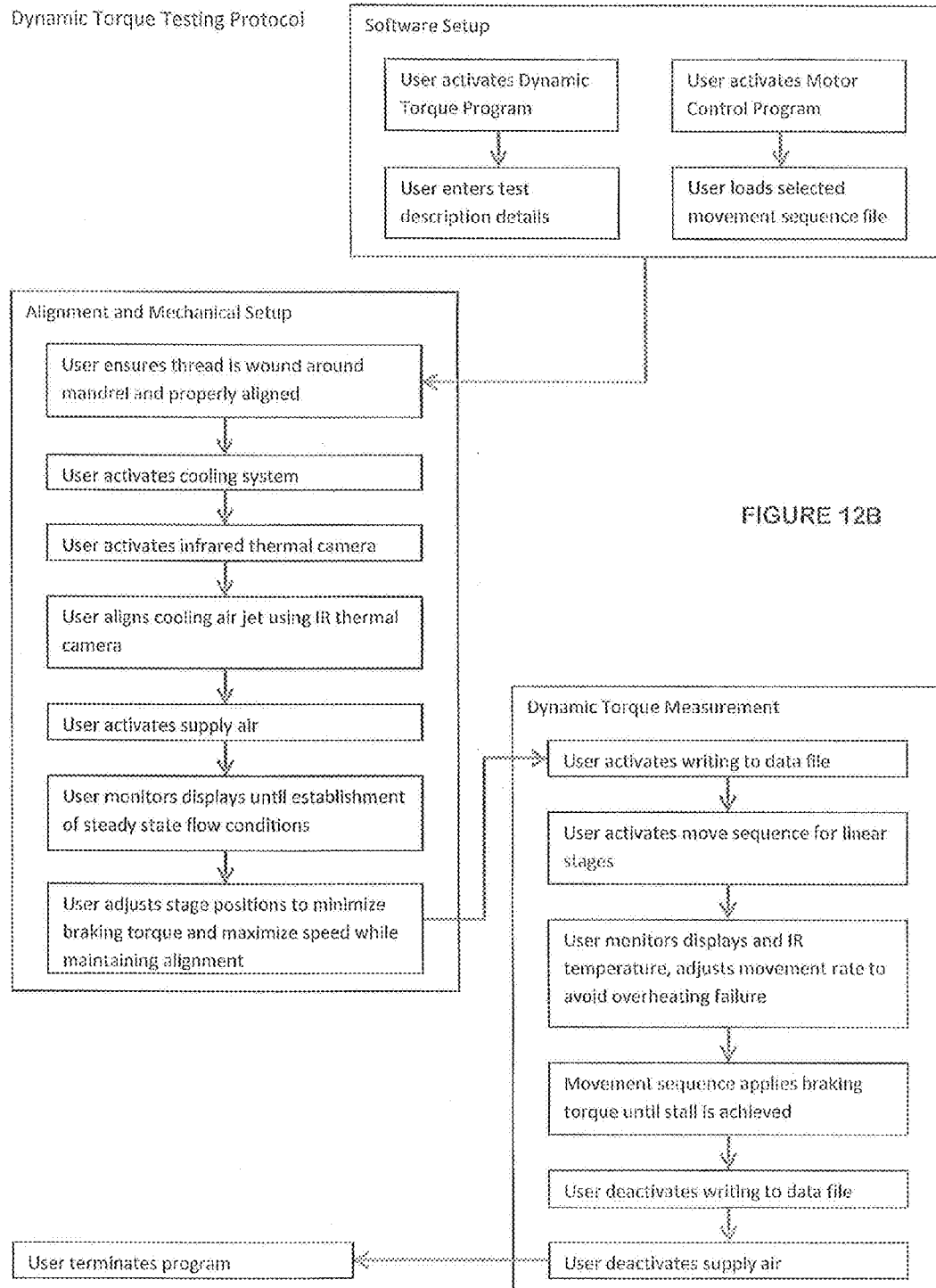
FIG. 12B is a flow diagram setting forth the dynamic torque testing protocol applicable to the data acquisition flow diagram of FIG. 12A.
Figure 12C:
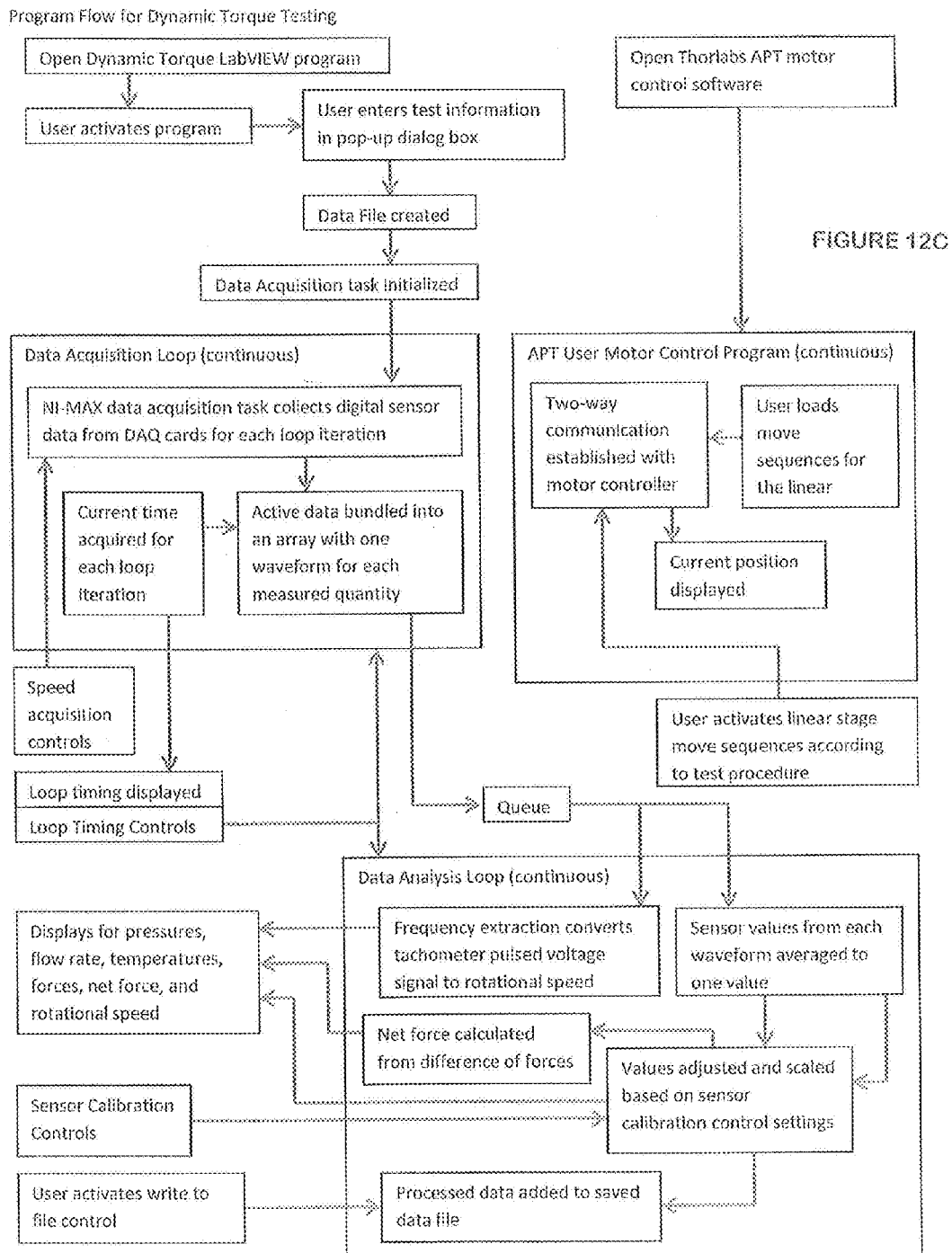
FIG. 12C is a program flow chart for dynamic torque testing illustrating in greater detail the data acquisition and analysis thereof associated with the flow diagrams of FIGS. 12A and 12B.

FIGS. 12A, 12B and 12C illustrate in greater detail the flow diagrams associated with the collection of data associated with dynamic torque, the testing protocol for determining dynamic torque and the program flow for dynamic torque testing. FIG. 12A sets forth the identification of the various sensors associated with the acquisition of data which is to be reviewed, examined, stored and manipulated for the determination of dynamic torque. FIG. 12B summarizes the system set-up as it applies to alignment and arrangement of the sensors and the protocol for set up of the sensors. These features then provide a testing protocol wherein the measurements are acquired. Importantly, the measurements are associated with the movement sequences of the linear stages or force sensors 50 and 52. The movement sequence of the force sensors in combination with the other data is then recorded as set forth in the exemplary graphs. FIG. 12C is a flow diagram which more fully illustrates the sequence of the steps which are performed to provide the recordable data output.

EXAMPLE 2

Stall Torque and Bearing Resistance

Measurement of handpiece characteristics when the handpiece is not operating at a high rotational speed can be important in characterizing its performance. However, a change in the apparatus configuration is required from the method used for dynamic torque testing.

a. As depicted in FIG. 9 the mandrel configuration for the dynamic torque setup is modified as illustrated in FIG. 9. A mandrel 27 is modified to permit the attachment of the thread 29 fixedly to the flange 33 of the mandrel drum or body 35. In this method, the thread 29 is evenly wound along the modified mandrel 27 (multiple time (5 of more) while pressure is applied by control of mount 60.

b. Retracting the line mount or at stage 60 at a low rate unwinds the thread 29 from the mandrel 27 through two complete rotations while maintaining effective stall and measuring force and air flow characteristics.

c. Averaging over complete rotations accounts for variations in torque due to rotor position in the air turbine handpiece head. For air turbine handpieces, the measured supply air characteristics can be used to calculate additional parameters of interest simultaneously at any point in the test or averaged across a revolution.

d. Following the previous steps (a-c) with no supply pressure allows estimation of tool bearing resistance which can indicate handpiece damage or wear.

e. Reversing the direction of rotation of the stall torque test (advancing the stage in the same direction that the handpiece is attempting to rotate) allows the determination of the reverse stall torque. Reverse stall torque is related to the forward stall torque and bearing resistance of the handpiece.

Figure 10:
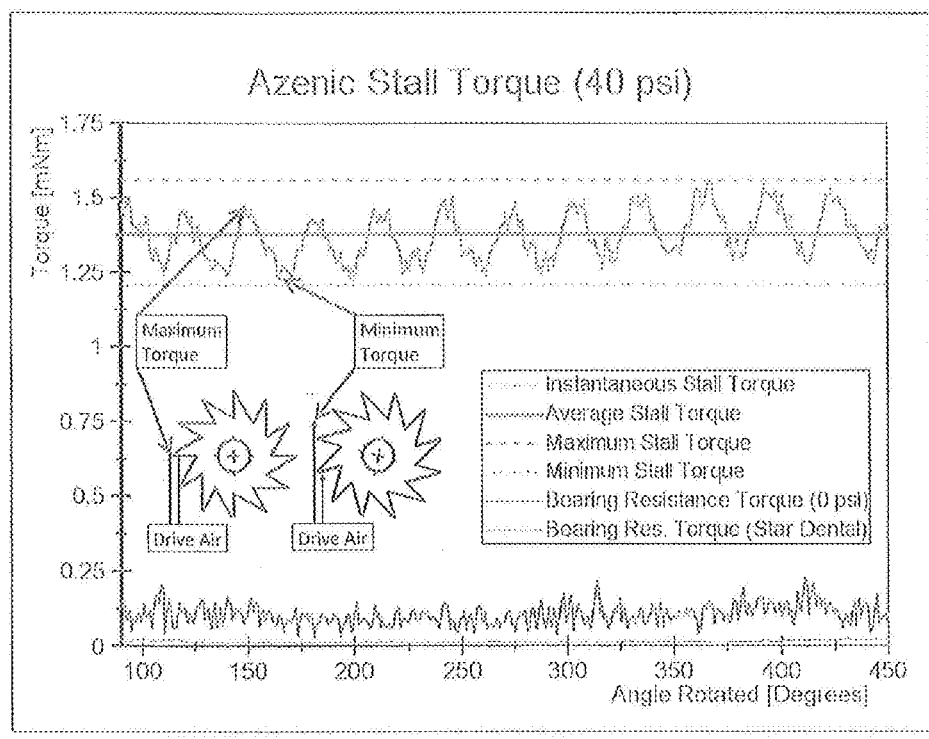
FIG. 10 is a plot depicting torque for a dental air turbine handpiece depicting various aspects of torque including stall torque.
Figure 13A:
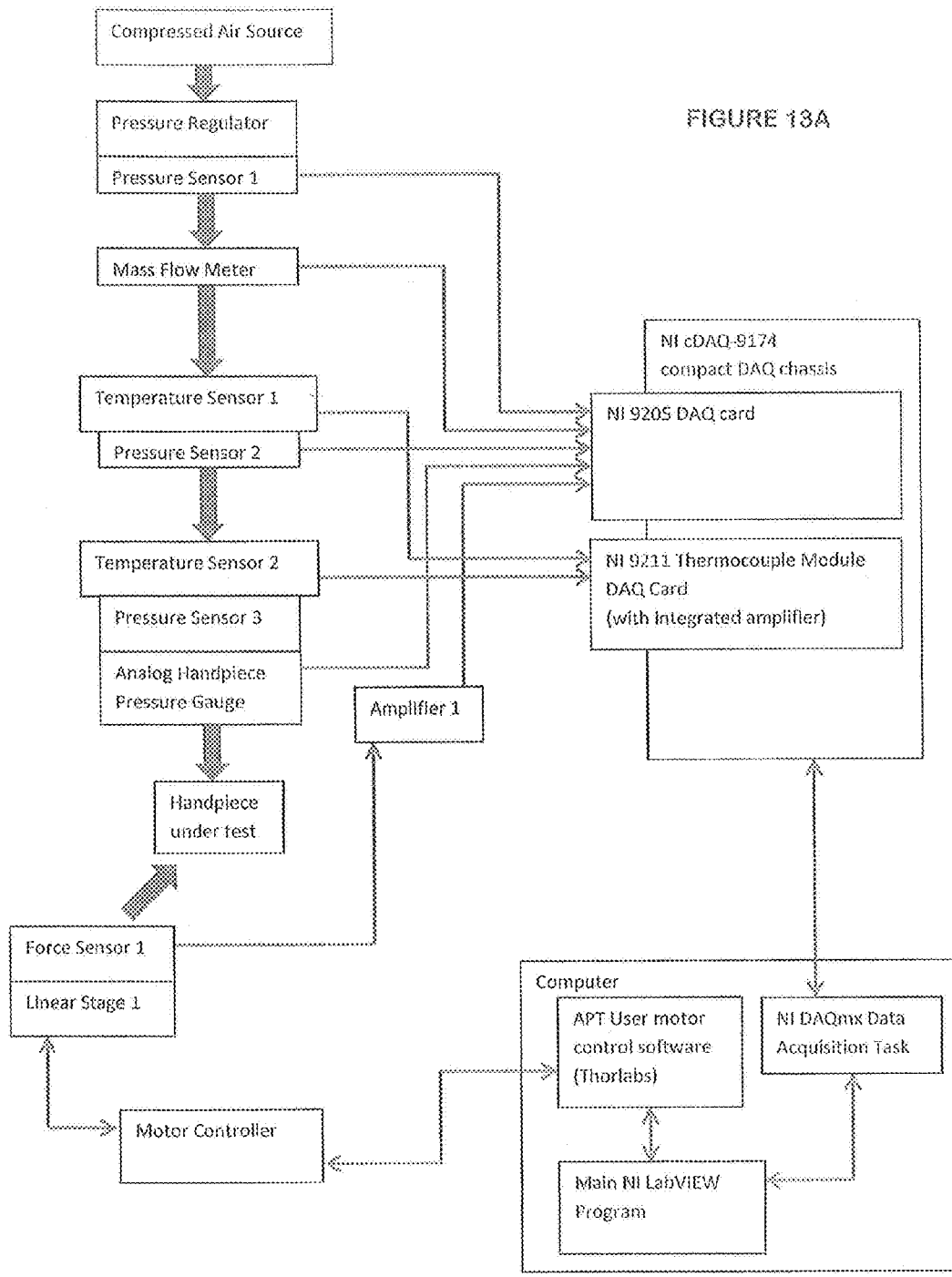
FIG. 13A is a data acquisition flow diagram associated with the determination of stall torque.
Figure 13B:
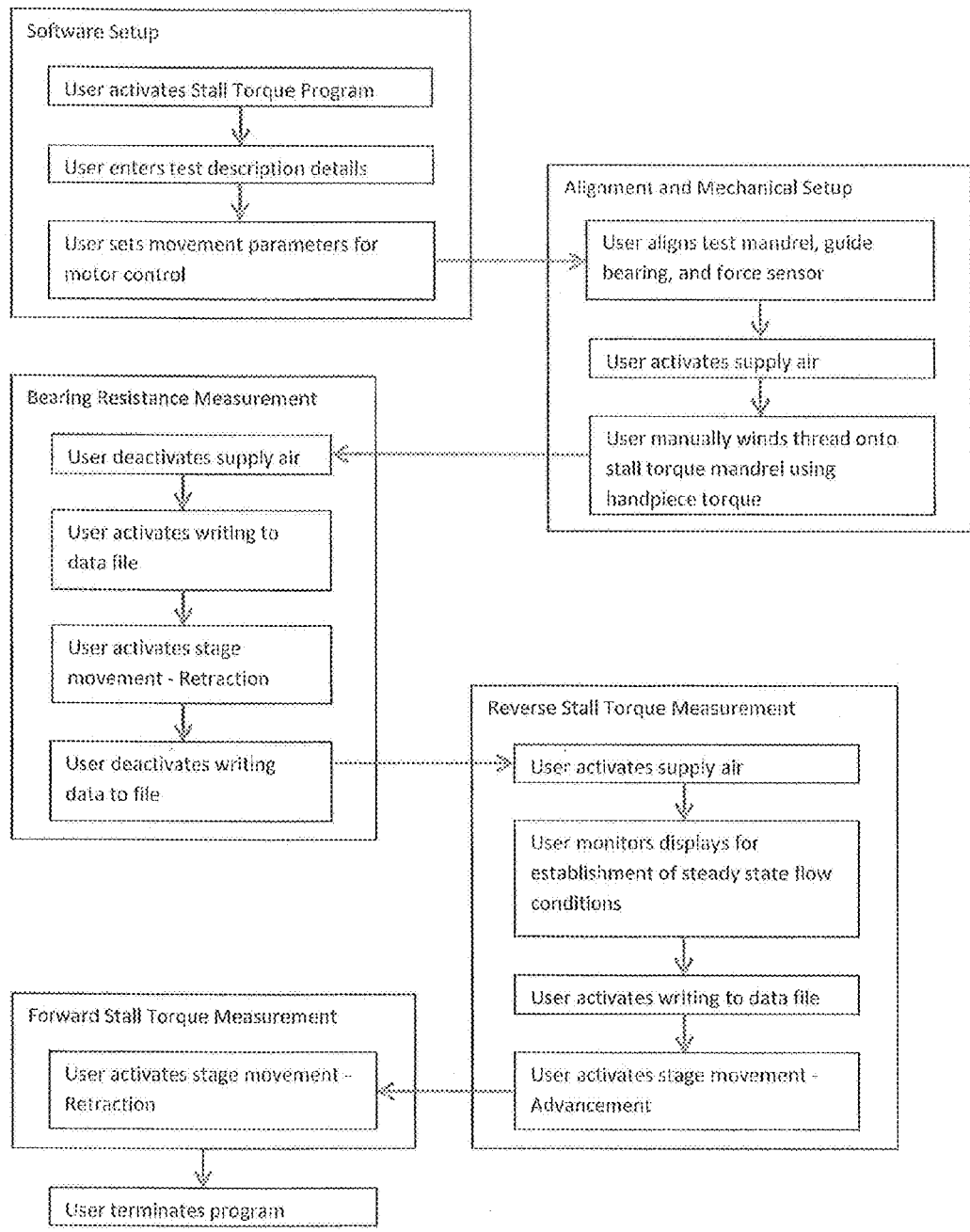
FIG. 13B is a flow diagram setting forth the stall torque testing protocol utilizing apparatus for, example, of the type depicted in FIG. 9.
Figure 13C:
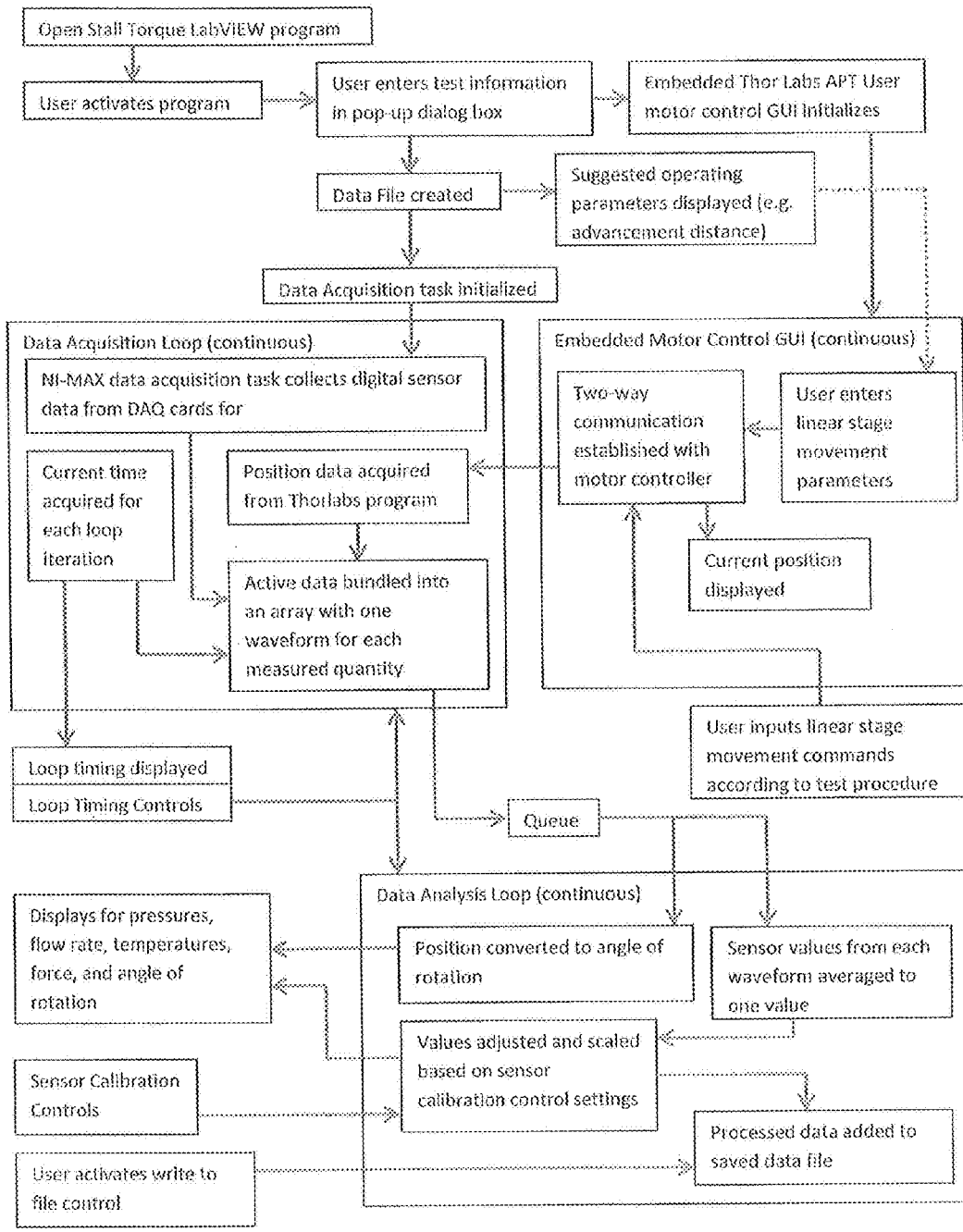
FIG. 13C is a flow diagram setting forth the stall torque testing protocol as associated with the flow diagrams of FIGS. 13A and 13B.

FIGS. 13A, 131B and 13C relate to the flow diagram for data acquisition, testing protocol and program flow with respect to stall torque. Note that only one force sensor is required with respect to conduct of this particular protocol as explained heretofore and depicted in the figures. FIG. 13A thus describes the data acquisition program implemented as well as the computer hardware and software arrangement. FIG. 13B illustrates the protocol including the software set-up which mandates the mechanical set up that when analyzed can result in bearing resistance associated with the tool under investigation, reverse stall torque measurements as well as forward stall torque measurements of the type depicted in FIG. 10, for example. The specific software flow diagram thus as set forth in FIG. 13C details the successive steps in the operation of the hardware in order to collect measurable data and display the data in a useful form.

f. FIG. 10 shows an example of a stall torque and bearing resistance plot. FIG. 10 provides a plot relating to stall torque for a dental turbine handpiece. Stall torque is depicted on the X axis or vertical axis versus a single rotation of the mandrel. The plot shows one complete rotation of the mandrel. Bearing resistance, measured with supply air turned off, is also shown in the plot. The inset diagram illustrates how the position of the rotor blades relative to the stream of drive air produces the saw tooth plot of the torque versus the angle of rotation. In addition, the various types of torque are indicated in the plot.

EXAMPLE 3

Free Running Speed and Supply Air

To test the relationship of various air flow parameters including supply pressure and flow rate on air turbine handpiece performance, the apparatus can be modified to perform a free running speed test.

a. In this method, no thread is used and data are not collected from the force sensors. Instead, the rotational speed, supply pressure, pressure at the handpiece, mass flow rate and temperature are recorded as pressure is increased from zero to the recommended operating pressure or higher.

b. Pressure is maintained at each desired value until steady state temperature conditions are reached.

c. Analysis and modeling based on this data are used to calculate additional handpiece performance characteristics and modeling equations.

Various other analytical comparisons based on the data gathered with the test apparatus of the invention can be performed and comparisons can be made between tools designed for similar purposes to evaluate whether they may meet standards, whether they are efficient and whether the design of the tool is considered adequate for the purpose for which it is designed.

Thus, while there has been set forth representative embodiments of the invention, the invention is to be limited only by the following claims and equivalents thereof.

What is claimed is:

1. A tool evaluation and testing assembly for securing operational data for fluid driven tool devices having a rotary drive output mechanism capable of driving a drive shaft of a tool, said assembly comprising, in combination:
   a support mount for holding a tool device in a generally fixed orientation;
   a compressed gas fluid supply source;
   a gas fluid conduit for transport of compressed gas fluid from the supply source to a tool device fluid inlet of a said tool device supported by said mount, said conduit including, in seriatim, downstream from said fluid supply source:
      a) a fluid pressure regulator,
      b) a first pressure sensor,
      c) a fluid mass flow metering sensor,
      d) a second pressure sensor
      e) a fluid temperature sensor, and
      f) a third pressure sensor;
   a mandrel for attachment to a mechanical collet mechanism of a said tool device, said mandrel including a linear shaft for engaging a said collet mechanism, a generally cylindrical body coaxial with said shaft, said body construction characterized by a generally smooth outer surface and capable of engaging an elongate cord wrapped around said body, said cord having first and second opposite ends extending from the body surface; and
   first and second force sensor characterized for positioning on opposite sides of said mandrel body, said force sensors each mounted on an adjustable platform for providing and connected respectively to a separate end of said cord, said sensor mounts adjustable tensile force on a said cord attached to each said force sensor mounted on the platform supporting the said force sensor;
   a mandrel speed sensor mounted proximate to the mandrel for sensing rotation speed of said mandrel; and
   data recording devices for recording data from said sensors.

2. The assembly of claim 1 including a data processor for converting the data collected from selected said sensors to a ratio for a said tool device of one or more characteristics selected from the group consisting of:
   a) a torque to speed,
   b) power to speed,
   c) efficiency to speed, and
   d) torque to degree of rotation tool motor turbine blade.

3. The assembly of claim 1 further including at least one guide for said cord positioned intermediate said mandrel body and a said force sensor.

4. The assembly of claim 1 further including a gas cooling source positioned to direct5 cooling gas upon said mandrel body.

5. The assembly of claim 1 further including a temperature sensor juxtaposed to sense the temperature the Mandrel body.

6. The assembly of claim 1 wherein said mandrel includes a cord attachment for attaching one end of said cord, with the opposite end of a said cord attached to a said force sensor with said cord wrapped around the cylindrical body member multiple times.

7. The assembly of claim 1 including a data processor for converting data collected from selected said sensors for a said tool device to provide a record of one or more characteristics selected from a group consisting of:
   a) instantaneous stall torque,
   b) average stall torque,
   c) maximum stall torque,
   d) minimum stall torque,
   e) bearing resistance and;
   f) bearing resistance torque.

8. The assembly of claim 1 wherein the said tool mount is adjustable in at least two axial directions.

\* \* \* \* \*